United States Patent
Fulkerson et al.

(10) Patent No.: US 8,535,522 B2
(45) Date of Patent: *Sep. 17, 2013

(54) SYSTEM AND METHOD FOR DETECTION OF DISCONNECTION IN AN EXTRACORPOREAL BLOOD CIRCUIT

(75) Inventors: Barry Neil Fulkerson, Longmont, CO (US); James R. Braig, Piedmont, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 321 days.

This patent is subject to a terminal disclaimer.

(21) Appl. No.: 12/705,054

(22) Filed: Feb. 12, 2010

(65) Prior Publication Data

US 2010/0234786 A1     Sep. 16, 2010

Related U.S. Application Data

(60) Provisional application No. 61/151,912, filed on Feb. 12, 2009.

(51) Int. Cl.
| | |
|---|---|
| *B01D 61/32* | (2006.01) |
| *B01D 61/28* | (2006.01) |
| *B01D 61/30* | (2006.01) |
| *A61M 1/14* | (2006.01) |

(52) U.S. Cl.
USPC .......... 210/143; 210/85; 210/90; 210/97; 210/103; 210/134; 210/141; 210/321.6; 604/4.01; 604/30; 604/65; 604/67

(58) Field of Classification Search
USPC .......... 210/85, 90, 97, 103, 109, 134, 141, 210/143, 321.6; 604/4.01, 30, 65, 67
See application file for complete search history.

(56) References Cited

U.S. PATENT DOCUMENTS

| | | |
|---|---|---|
| 2,328,381 A | 8/1943 | Jaffe |
| 4,071,444 A | 1/1978 | Ash et al. |

(Continued)

FOREIGN PATENT DOCUMENTS

| | | |
|---|---|---|
| WO | 2009073567 | 6/2009 |
| WO | 2010114932 | 7/2010 |

OTHER PUBLICATIONS

Renal Solutions, Inc., "The Allient Sorbent Hemodialysis System Operator Manual", RSI Part No. 207460, Revision C, 2008.

(Continued)

*Primary Examiner* — John Kim
(74) *Attorney, Agent, or Firm* — Novel IP (57) ABSTRACT

The present invention is directed to a dialysis system with a disconnection monitor for determining if a blood line connection to a patient has been disconnected. It includes a blood circuit in fluid communication with a patient and a dialysis circuit, a pressure transducer for generating a signal indicative of a pulse signal in the blood circuit, a cardiac reference signal generator for generating a signal indicative of the patient's pulse and a disconnection monitor. The disconnection monitor includes a pressure transducer data receiver for receiving the signal indicative of the pulse signal in the blood circuit, a cardiac reference signal receiver for receiving the signal indicative of the patient's pulse, and a processor for cross-correlating the signal indicative of the pulse signal in the blood circuit and the signal indicative of the patient's pulse to generate data indicative of a disconnection of the blood line connection to the patient.

20 Claims, 3 Drawing Sheets

(56) References Cited

U.S. PATENT DOCUMENTS

| | | | |
|---|---|---|---|
| 4,083,777 | A | 4/1978 | Hutchisson |
| 4,113,614 | A | 9/1978 | Rollo et al. |
| 4,348,283 | A | 9/1982 | Ash |
| 4,368,737 | A | 1/1983 | Ash |
| 4,387,777 | A | 6/1983 | Ash |
| 4,397,189 | A | 8/1983 | Johnson et al. |
| 4,402,694 | A | 9/1983 | Ash et al. |
| 4,403,984 | A | 9/1983 | Ash et al. |
| 4,413,988 | A | 11/1983 | Handt et al. |
| 4,469,593 | A | 9/1984 | Ishihara et al. |
| 4,477,342 | A | 10/1984 | Allan et al. |
| 4,498,902 | A | 2/1985 | Ash et al. |
| 4,559,039 | A | 12/1985 | Ash et al. |
| 4,581,141 | A | 4/1986 | Ash |
| 4,596,550 | A | 6/1986 | Troutner |
| 4,599,055 | A | 7/1986 | Dykstra |
| 4,606,826 | A | 8/1986 | Sano et al. |
| 4,661,246 | A | 4/1987 | Ash |
| 4,666,598 | A | 5/1987 | Heath et al. |
| 4,680,122 | A | 7/1987 | Barone |
| 4,683,053 | A | 7/1987 | Polaschegg |
| 4,740,755 | A | 4/1988 | Ogawa |
| 4,762,618 | A | 8/1988 | Gummesson et al. |
| 4,777,953 | A | 10/1988 | Ash et al. |
| 4,854,322 | A | 8/1989 | Ash et al. |
| 4,861,242 | A | 8/1989 | Finsterwald |
| 4,909,713 | A | 3/1990 | Finsterwald et al. |
| 4,914,819 | A | 4/1990 | Ash |
| 4,950,244 | A | 8/1990 | Fellingham et al. |
| 4,990,258 | A | 2/1991 | Bjare et al. |
| 4,995,268 | A | 2/1991 | Ash et al. |
| 4,997,570 | A | 3/1991 | Polaschegg |
| 5,002,054 | A | 3/1991 | Ash et al. |
| 5,011,607 | A | 4/1991 | Shinzato |
| 5,032,261 | A | 7/1991 | Pyper |
| 5,100,554 | A | 3/1992 | Polaschegg |
| 5,114,580 | A | 5/1992 | Ahmad et al. |
| 5,147,613 | A | 9/1992 | Heilmann et al. |
| 5,198,335 | A | 3/1993 | Sekikawa et al. |
| 5,211,643 | A | 5/1993 | Reinhardt et al. |
| 5,230,341 | A | 7/1993 | Polaschegg |
| 5,277,820 | A | 1/1994 | Ash |
| 5,295,505 | A | 3/1994 | Polaschegg et al. |
| 5,304,349 | A | 4/1994 | Polaschegg |
| 5,308,315 | A | 5/1994 | Khuri et al. |
| 5,322,519 | A | 6/1994 | Ash |
| 5,385,005 | A | 1/1995 | Ash |
| D355,816 | S | 2/1995 | Ash |
| 5,405,315 | A | 4/1995 | Khuri et al. |
| 5,441,636 | A | 8/1995 | Chevallet et al. |
| 5,445,630 | A | 8/1995 | Richmond |
| 5,460,493 | A | 10/1995 | Deniega et al. |
| 5,476,444 | A | 12/1995 | Keeling et al. |
| D370,531 | S | 6/1996 | Ash et al. |
| 5,536,412 | A | 7/1996 | Ash |
| 5,540,265 | A | 7/1996 | Polaschegg et al. |
| 5,577,891 | A | 11/1996 | Loughnane et al. |
| 5,580,460 | A | 12/1996 | Polaschegg |
| 5,614,677 | A | 3/1997 | Wamsiedler et al. |
| 5,616,305 | A | 4/1997 | Mathieu |
| 5,624,551 | A | 4/1997 | Baumann et al. |
| 5,629,871 | A | 5/1997 | Love et al. |
| 5,632,897 | A | 5/1997 | Mathieu |
| 5,644,285 | A | 7/1997 | Maurer |
| 5,674,390 | A | 10/1997 | Matthews et al. |
| 5,679,245 | A | 10/1997 | Manica |
| 5,693,008 | A | 12/1997 | Brugger et al. |
| 5,698,083 | A | 12/1997 | Glass |
| 5,711,883 | A | 1/1998 | Folden et al. |
| 5,713,850 | A | 2/1998 | Heilmann et al. |
| 5,725,773 | A | 3/1998 | Polaschegg |
| 5,744,027 | A | 4/1998 | Connell et al. |
| 5,782,796 | A | 7/1998 | Din et al. |
| 5,794,669 | A | 8/1998 | Polaschegg et al. |
| 5,858,186 | A | 1/1999 | Glass |
| 5,906,978 | A | 5/1999 | Ash |
| 5,919,369 | A | 7/1999 | Ash |
| 5,945,343 | A | 8/1999 | Munkholm |
| 5,947,953 | A | 9/1999 | Ash et al. |
| 5,951,870 | A | 9/1999 | Utterberg |
| 5,989,423 | A | 11/1999 | Kamen et al. |
| 5,989,438 | A | 11/1999 | Fumiyama |
| 6,042,561 | A | 3/2000 | Ash et al. |
| 6,086,753 | A | 7/2000 | Ericson et al. |
| 6,156,007 | A | 12/2000 | Ash |
| 6,190,349 | B1 | 2/2001 | Ash et al. |
| 6,217,540 | B1 | 4/2001 | Yazawa et al. |
| 6,234,989 | B1 | 5/2001 | Brierton et al. |
| 6,254,567 | B1 | 7/2001 | Treu et al. |
| 6,264,680 | B1 | 7/2001 | Ash |
| 6,280,406 | B1 | 8/2001 | Dolecek et al. |
| 6,284,131 | B1 | 9/2001 | Hogard et al. |
| 6,287,516 | B1 | 9/2001 | Matson et al. |
| 6,303,036 | B1 | 10/2001 | Collins et al. |
| 6,332,985 | B1 | 12/2001 | Sherman et al. |
| 6,348,162 | B1 | 2/2002 | Ash |
| 6,409,699 | B1 | 6/2002 | Ash |
| 6,416,293 | B1 | 7/2002 | Bouchard et al. |
| 6,468,427 | B1 | 10/2002 | Frey |
| 6,471,872 | B2 | 10/2002 | Kitaevich et al. |
| 6,497,675 | B1 | 12/2002 | Davankov |
| 6,551,513 | B2 | 4/2003 | Nikaido et al. |
| 6,554,789 | B1 | 4/2003 | Brugger et al. |
| 6,572,576 | B2 | 6/2003 | Brugger et al. |
| 6,572,641 | B2 | 6/2003 | Brugger et al. |
| 6,579,253 | B1 | 6/2003 | Brugger et al. |
| 6,579,460 | B1 | 6/2003 | Willis et al. |
| 6,582,385 | B2 | 6/2003 | Brugger et al. |
| 6,589,482 | B1 | 7/2003 | Brugger et al. |
| 6,595,943 | B1 | 7/2003 | Burbank |
| 6,623,470 | B2 | 9/2003 | Munis et al. |
| 6,627,164 | B1 | 9/2003 | Wong |
| 6,638,477 | B1 | 10/2003 | Treu et al. |
| 6,638,478 | B1 | 10/2003 | Treu et al. |
| 6,649,063 | B2 | 11/2003 | Brugger et al. |
| 6,653,841 | B1 | 11/2003 | Koerdt et al. |
| 6,673,314 | B1 | 1/2004 | Burbank et al. |
| 6,695,803 | B1 | 2/2004 | Robinson et al. |
| 6,702,561 | B2 | 3/2004 | Stillig et al. |
| 6,730,266 | B2 | 5/2004 | Matson et al. |
| 6,743,193 | B2 | 6/2004 | Brugger et al. |
| 6,764,460 | B2 | 7/2004 | Dolecek et al. |
| 6,773,412 | B2 | 8/2004 | O'Mahony et al. |
| 6,818,196 | B2 | 11/2004 | Wong |
| 6,830,553 | B1 | 12/2004 | Burbank et al. |
| 6,841,172 | B1 | 1/2005 | Ash |
| 6,852,090 | B2 | 2/2005 | Burbank et al. |
| 6,872,346 | B2 | 3/2005 | Stillig |
| 6,878,283 | B2 | 4/2005 | Thompson |
| 6,899,691 | B2 | 5/2005 | Bainbridge et al. |
| 6,923,782 | B2 | 8/2005 | O'Mahony et al. |
| 6,955,655 | B2 | 10/2005 | Burbank et al. |
| 6,958,049 | B1 | 10/2005 | Ash |
| 6,960,179 | B2 | 11/2005 | Gura |
| 6,960,328 | B2 | 11/2005 | Bortun et al. |
| 6,979,309 | B2 | 12/2005 | Burbank et al. |
| 7,004,924 | B1 | 2/2006 | Brugger et al. |
| 7,033,498 | B2 | 4/2006 | Wong |
| 7,040,142 | B2 | 5/2006 | Burbank |
| 7,087,033 | B2 | 8/2006 | Brugger et al. |
| 7,101,519 | B2 | 9/2006 | Wong |
| 7,112,273 | B2 | 9/2006 | Weigel et al. |
| 7,115,095 | B2 | 10/2006 | Eigler et al. |
| 7,135,156 | B2 | 11/2006 | Hai et al. |
| 7,144,386 | B2 | 12/2006 | Korkor et al. |
| 7,147,613 | B2 | 12/2006 | Burbank et al. |
| 7,169,303 | B2 | 1/2007 | Sullivan et al. |
| 7,175,809 | B2 | 2/2007 | Gelfand et al. |
| 7,214,312 | B2 | 5/2007 | Brugger et al. |
| 7,226,538 | B2 | 6/2007 | Brugger et al. |
| 7,241,272 | B2 | 7/2007 | Karoor et al. |
| 7,252,767 | B2 | 8/2007 | Bortun et al. |
| 7,267,658 | B2 | 9/2007 | Treu et al. |
| 7,273,465 | B2 | 9/2007 | Ash |

| | | |
|---|---|---|
| 7,276,042 B2 | 10/2007 | Polaschegg et al. |
| 7,300,413 B2 | 11/2007 | Burbank et al. |
| 7,309,323 B2 | 12/2007 | Gura et al. |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,494,590 B2 | 2/2009 | Felding et al. |
| 7,648,476 B2 | 1/2010 | Bock et al. |
| 7,713,226 B2 | 5/2010 | Ash et al. |
| 7,780,619 B2 | 8/2010 | Brugger et al. |
| 7,794,141 B2 | 9/2010 | Perry et al. |
| 7,873,489 B2 | 1/2011 | Dolgos et al. |
| 7,886,611 B2 | 2/2011 | O'Mahony et al. |
| 7,901,376 B2 | 3/2011 | Steck et al. |
| 7,922,898 B2 | 4/2011 | Jonsson et al. |
| 7,922,899 B2 | 4/2011 | Vasta et al. |
| 7,981,280 B2 | 7/2011 | Carr et al. |
| 7,998,101 B2 | 8/2011 | Ash |
| 8,021,319 B2 | 9/2011 | Delnevo et al. |
| 8,034,235 B2 | 10/2011 | Rohde et al. |
| 8,062,513 B2 | 11/2011 | Yu et al. |
| 8,066,658 B2 | 11/2011 | Karoor et al. |
| 8,070,707 B2 | 12/2011 | Gelfand et al. |
| 8,075,509 B2 | 12/2011 | Molducci et al. |
| 8,078,333 B2 | 12/2011 | Kienman et al. |
| 8,105,260 B2 | 1/2012 | Tonelli et al. |
| 2002/0068364 A1 | 6/2002 | Arai et al. |
| 2002/0085951 A1 | 7/2002 | Gelfand et al. |
| 2003/0128125 A1 | 7/2003 | Burbank et al. |
| 2005/0070837 A1 | 3/2005 | Ferrarini et al. |
| 2005/0131332 A1 | 6/2005 | Kelly et al. |
| 2005/0133439 A1 | 6/2005 | Blickhan |
| 2006/0122552 A1 | 6/2006 | O'Mahony |
| 2007/0112297 A1 | 5/2007 | Plahey et al. |
| 2007/0158249 A1 | 7/2007 | Ash |
| 2007/0158268 A1 | 7/2007 | DeComo |
| 2007/0161113 A1 | 7/2007 | Ash |
| 2007/0213654 A1 | 9/2007 | Lundtveit et al. |
| 2008/0041136 A1 | 2/2008 | Kopelman et al. |
| 2008/0041792 A1 | 2/2008 | Crnkovich et al. |
| 2008/0065006 A1 | 3/2008 | Roger et al. |
| 2008/0149563 A1 | 6/2008 | Ash |
| 2008/0195021 A1 | 8/2008 | Roger et al. |
| 2008/0195060 A1 | 8/2008 | Roger et al. |
| 2008/0230450 A1 | 9/2008 | Burbank et al. |
| 2009/0079578 A1 | 3/2009 | Dvorsky et al. |
| 2009/0080757 A1 | 3/2009 | Roger et al. |
| 2009/0082646 A1 | 3/2009 | Bouton |
| 2009/0082647 A1 | 3/2009 | Busby |
| 2009/0082649 A1 | 3/2009 | Muller et al. |
| 2009/0082653 A1 | 3/2009 | Rohde |
| 2009/0082676 A1 | 3/2009 | Bennison |
| 2009/0095679 A1 | 4/2009 | Demers et al. |
| 2009/0105627 A1 | 4/2009 | Rohde |
| 2009/0113335 A1 | 4/2009 | Sandoe et al. |
| 2009/0312694 A1 | 12/2009 | Bedingfield et al. |
| 2010/0312161 A1 | 12/2010 | Jonsson et al. |
| 2010/0326916 A1 | 12/2010 | Wrazel et al. |
| 2011/0000830 A1 | 1/2011 | Ikeda |
| 2011/0009799 A1 | 1/2011 | Mullick et al. |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani et al. |
| 2011/0054352 A1 | 3/2011 | Ko et al. |
| 2011/0092907 A1 | 4/2011 | Krogh et al. |
| 2011/0093294 A1 | 4/2011 | Elahi et al. |
| 2011/0098545 A1 | 4/2011 | Ross et al. |
| 2011/0098624 A1 | 4/2011 | McCotter et al. |
| 2011/0098625 A1 | 4/2011 | Masala et al. |
| 2011/0098635 A1 | 4/2011 | Helmore et al. |
| 2011/0105877 A1 | 5/2011 | Wilt et al. |
| 2011/0105981 A1 | 5/2011 | Wagner et al. |
| 2011/0105983 A1 | 5/2011 | Kelly et al. |
| 2011/0105984 A1 | 5/2011 | Patel et al. |
| 2011/0106002 A1 | 5/2011 | Helmore et al. |
| 2011/0106047 A1 | 5/2011 | Burbank et al. |
| 2011/0106466 A1 | 5/2011 | Furmanski et al. |
| 2011/0107251 A1 | 5/2011 | Guaitoli et al. |
| 2011/0108482 A1 | 5/2011 | Lovell |
| 2011/0125073 A1 | 5/2011 | Rambod et al. |
| 2011/0126714 A1 | 6/2011 | Brugger et al. |
| 2011/0132838 A1 | 6/2011 | Curtis et al. |
| 2011/0132841 A1 | 6/2011 | Rohde et al. |
| 2011/0137224 A1 | 6/2011 | Ibragimov |
| 2011/0137264 A1 | 6/2011 | Chelak |
| 2011/0139704 A1 | 6/2011 | Choi et al. |
| 2011/0140896 A1 | 6/2011 | Menzel |
| 2011/0141116 A1 | 6/2011 | Dalesch et al. |
| 2011/0152739 A1 | 6/2011 | Roncadi et al. |
| 2011/0155657 A1 | 6/2011 | Collins et al. |
| 2011/0160649 A1 | 6/2011 | Pan |
| 2011/0166507 A1 | 7/2011 | Childers et al. |
| 2011/0168614 A1 | 7/2011 | Pouchoulin et al. |
| 2011/0171713 A1 | 7/2011 | Bluchel et al. |
| 2011/0189048 A1 | 8/2011 | Curtis et al. |
| 2011/0208072 A1 | 8/2011 | Pfeiffer et al. |
| 2011/0208106 A1 | 8/2011 | Levin et al. |
| 2011/0213289 A1 | 9/2011 | Toyoda et al. |
| 2011/0218475 A1 | 9/2011 | Brugger et al. |
| 2011/0218487 A1 | 9/2011 | Shang et al. |
| 2011/0226680 A1 | 9/2011 | Jonsson et al. |
| 2011/0230814 A1 | 9/2011 | Kopperschmidt et al. |
| 2011/0237997 A1 | 9/2011 | Beden et al. |
| 2011/0237998 A1 | 9/2011 | Wariar et al. |
| 2011/0240537 A1 | 10/2011 | Ferrarini et al. |
| 2011/0240555 A1 | 10/2011 | Ficheux et al. |
| 2011/0269167 A1 | 11/2011 | Bene |
| 2011/0272352 A1 | 11/2011 | Braig |
| 2011/0275984 A1 | 11/2011 | Biewer et al. |
| 2011/0284464 A1 | 11/2011 | Roncadi et al. |
| 2011/0297593 A1 | 12/2011 | Kelly et al. |
| 2011/0297598 A1 | 12/2011 | Lo et al. |
| 2011/0297599 A1 | 12/2011 | Lo et al. |
| 2011/0300010 A1 | 12/2011 | Jarnagin et al. |
| 2011/0300230 A1 | 12/2011 | Peterson et al. |
| 2011/0303588 A1 | 12/2011 | Kelly et al. |
| 2011/0303590 A1 | 12/2011 | Childers et al. |
| 2011/0303598 A1 | 12/2011 | Lo et al. |
| 2011/0309019 A1 | 12/2011 | Ahrens |
| 2011/0315611 A1* | 12/2011 | Fulkerson et al. ............ 210/96.2 |
| 2012/0010554 A1 | 1/2012 | Vantard et al. |
| 2012/0018377 A1 | 1/2012 | Tsukamoto |
| 2012/0018378 A1 | 1/2012 | Kelly et al. |
| 2012/0022440 A1 | 1/2012 | Childers et al. |
| 2012/0029324 A1 | 2/2012 | Akonur et al. |
| 2012/0029937 A1 | 2/2012 | Neftel et al. |
| 2012/0031826 A1 | 2/2012 | Childers et al. |
| 2012/0035534 A1 | 2/2012 | Yu et al. |
| 2012/0037550 A1 | 2/2012 | Childers et al. |
| 2012/0043279 A1 | 2/2012 | Kelly et al. |
| 2012/0065567 A1 | 3/2012 | Zarate |
| 2012/0075266 A1 | 3/2012 | Shimizu et al. |

OTHER PUBLICATIONS

Reyes et al., "Acid-Base Derangements During Sorbent Regenerative Hemodialysis in Mechanically Ventilated Patients", Critical Care Medicine, vol. 19, No. 4, 1991, 554-559 (col. 2, lines 17-22).

Fresenius AG, "Acumen Acute Dialysis Machine Operating Instructions", Version 1.0, May 1996.

Cobe Laboratories, Inc., "CentrySystem 3 Dialysis Control Unit Operators Manual", Sep. 1988.

Renal Solutions, Inc., "The Allient Sorbent Hemodialysis System Home User Manual", 2006.

Renal Solutions, Inc., "The Allient Sorbent Hemodialysis System Operator Manual", RSI Part No. 206948, Revision G, 2008.

Fresenius USA, Inc., "Fresenius 2008H Hemodialysis Machine", Part No. 490005, Revision H, 1994-2001.

Renal Solutions, Inc., 510(K) for the SORB+ and HISORB+ Cartridges, Mar. 31, 2003.

CD Medical, Inc., "Operator's Manual Drake Willock 480 Ultrafiltration Control Single Patient Delivery System", 1988.

Renal Solutions, Inc., "Dialysate Tubing Set and Dialysate Reservoir Bag for the Allient Sorbent Hemodialysis System", Instructions, 2004.

NxStage Medical, Inc., "NxStage System One User's Guide", Software Version 4.3, Part 1 through Part 6-20, 2006.
NxStage Medical, Inc., "NxStage System One User's Guide", Software Version 4.3, Part 6-20 through Part C-17, 2006.
Renal Solutions, Inc., 510K for the Allient Sorbent Hemodialysis System, Dec. 17, 2004.
Manns et al., "The acu-men: A New Device for Continuous Renal Replacement Therapy in Acute Renal Failure", Kidney International, vol. 54 (1998), 268-274.
REDY® 2000 Operator's Manual (1991) (Sorbent cartridge-based hemodialysis system).
REDY® 2000 Service Manual (1989) (Sorbent cartridge-based hemodialysis system).
Seratron™ Dialysis Control System Operations Manual (cumulative 1980).
Ward et al., "Sorbent Dialysis Regenerated Dialysis Delivery Systems", Peritoneal Dialysis Bulletin, Chapter 8, 3(2): S41-S48 (Apr.-Jun. 1983).
Anthony J. Wing et al., "Dialysate Regeneration", Replacement of Renal Function by Dialysis, Chapter 17, 323-340 (William Drukker et al., eds., Martinus Nijhoff Publishers, 2nd ed., 1983).
Fresenius AG, "Acumen Acute Dialysis Machine Brief Operating Instructions", May 1996.
Renal Solutions, Special 510(k) Device Modification, Allient Sorbent Hemodialysis System, Mar. 15, 2007.
Renal Solutions, 510(K), Allient Sorbent Hemodialysis System, Dec. 2004.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections M.3 and M.4), Renal Solutions, Inc., Dec. 17, 2004.
Fresenius USA, Inc., Portions of Operator's Manual, Fresenius 2008H, Hemodialysis Machine, (Section 1), 2001, pp. 1-27.
Fresenius USA, Inc., Portions of Operator's Manual, Fresenius 2008H, Hemodialysis Machine, (Sections 2.1 to 2.6), 2001, pp. 29-54.
Fresenius USA, Inc., Portions of Operator's Manual, Fresenius 2008H, Hemodialysis Machine, (Sections 2.8 to 2.15), 2001, pp. 55-75.
Renal Solutions, Portions of the Allient Sorbent Hemodialysis System, Home User Manual, 2006, Chapters 1-3.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual Model 1500, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.

* cited by examiner

SYSTEM AND METHOD FOR DETECTION OF DISCONNECTION IN AN EXTRACORPOREAL BLOOD CIRCUIT

CROSS-REFERENCE

The present invention relies on U.S. Patent Provisional No. 61/151,912 filed on Feb. 12, 2009 for priority. The present invention is also related to a) U.S. patent application Ser. No. 12/575,450, filed on Oct. 7, 2009, b) U.S. patent application Ser. No. 12/575,449, filed on Oct. 7, 2009, c) U.S. patent application Ser. No. 12/355,102, filed on Jan. 16, 2009, d) U.S. patent application Ser. No. 12/355,128, filed on Jan. 16, 2009, e) U.S. patent application Ser. No. 12/351,969, filed on Jan. 12, 2009, f) U.S. patent application Ser. No. 12/324,924, filed on Nov. 28, 2008, g) U.S. patent application Ser. No. 12/210,080, filed on Sep. 12, 2008, h) U.S. patent application Ser. No. 12/238,055, filed on Sep. 25, 2008, i) U.S. patent application Ser. No. 12/237,914, filed on Sep. 25, 2008, j) U.S. patent application Ser. No. 12/249,090, filed on Oct. 10, 2008, k) U.S. patent application Ser. No. 12/245,397, filed on Oct. 3, 2008, l) U.S. patent application Ser. No. 12/610,032, filed on Oct. 30, 2009, and m) U.S. patent application Ser. No. 12/610,100, filed on Oct. 30, 2009. All of the aforementioned applications are herein incorporated by reference.

FIELD OF THE INVENTION

The present invention relates to medical apparatus and procedures. More particularly, the present invention relates to an apparatus and method for detection of disconnection in an extracorporeal blood circuit being used for any blood processing treatment routine.

BACKGROUND OF THE INVENTION

Vascular access for establishing an extracorporeal blood circuit is typically obtained by using a trans-dermal needle or a luer connected catheter. Usually blood processing treatment routines require establishment of extracorporeal blood circuits. Examples of blood processing treatment routines include continual renal replacement therapy such as hemodialysis wherein blood flows outside a patient's body via a set of tubes, commonly known as arterial supply line, to a dialyzer (artificial kidney) which removes waste products and excess fluids from it. Uncontaminated blood, then, flows back into the patient's body via a second set of tubes commonly referred to as venous return line.

An extracorporeal blood circuit might be disrupted while a blood processing treatment routine is in progress due to disconnection of a needle or a catheter providing vascular access. Such disruption may have serious and often fatal consequences. Needles corresponding to an arterial supply line or a venous return line of a blood circuit may disconnect due to numerous reasons, including the sudden movement of the patient undergoing the blood processing treatment. Disconnection of a supply line is relatively easy to detect by monitoring air in the supply line. In circumstances where a supply line disconnection remains undetected for some time, generally, only a slight blood loss occurs, which is equivalent to that caused by a small needle wound.

Disconnection of venous return line of an extracorporeal blood circuit is a much more alarming occurrence. The blood flow rate in most blood processing treatment routines such as hemodialysis is very high, typically around 300-400 ml/min. Hence, a disconnection of a venous return line results in blood being pumped out of a patient's body at a rapid rate. Multiple liters of hemorrhaging within a few minutes lead to serious injury and may cause death, if not detected and remedied immediately.

Detection of a return line disconnect is difficult, as most known methods are based on monitoring and detecting a change in pressure in the venous return line tubing. Return line disconnection usually occurs due to a needle pull out situation. Since, a needle typically offers the highest fluidic resistance in an extracorporeal blood circuit, a pressure change in the return line due to needle disconnect is not significant and cannot be detected easily. The pressure drop is also very low in cases where a catheter disconnects from a patient's body, causing a return line disconnection.

Hence, detection of a disconnection in a return venous blood circuit using pressure as an indicator or metric is unreliable and may result in serious injury. Further, methods using detection of air bubbles as an indication of a disconnect cannot be relied upon because a disconnect in a venous return line does not cause air to be drawn in the return line tubing.

One known method uses a detection of moisture at a needle site to detect the disconnection of a venous return line of an extracorporeal blood circuit. The method is based on an assumption that a needle pull out would cause a blood leak, thereby making the needle site wet. Various moisture sensing methods are available for use in the detection of moisture at a needle site. One such method employs optical spectrophotometry and another employs electrical conductivity measurement for moisture detection.

Moisture sensing methods require an additional apparatus, such as sensor elements to be fastened to a patient's body near the needle site. Further, such methods are based on the assumption that, after a needle pull, blood is pooled near the sensor element. However, in situations where the needle pull out is caused by a violent action, such as sudden rolling over of the patient while sleeping, the needle may cause blood flow at a distance from the sensor element. Hence, in such a situation, the moisture sensing method would provide a false negative and, at approximately 300 ml/min blood flow rate, excessive blood loss would occur in only a couple of minutes.

Another known method uses detection of certain signals from a patient's body for detection of disconnection of venous return line. This method detects changes in signals which are attributable to a needle pull out from a patient's body. One method measures electrical signals of a patient's heart through a return venous line of an extracorporeal blood circuit of the patient. In a needle pull out situation, the electrical signals are no longer detectable. This method takes advantage of the fact that blood is a good electrical conductor and the electrical signals generated by the patient's beating heart are conducted through blood carrying tubes as long as the extracorporeal blood circuit is unbroken.

However, the method fails in situations where a needle pull out occurs causing bleeding but the return venous line is intact due to fluid contact with the pool of blood. Also, efficiency of the method decreases due to the fact that the electrical activity of heart provides a very small electrical signal which, in a noisy electrical background, yields a low signal to noise ratio. Hence, loss of the signal or a failure to distinguish it from a noisy background may cause a false positive reading.

Consequently, there is need for an improved apparatus and method for detecting a disconnect in a venous return line. Further, there is also need for an apparatus and method which does not require any extra element, such as a moisture pad to be placed at the needle insertion site. Hence, there is need for an apparatus and method for detecting a disconnect in a venous return line of an extra corporeal blood circuit, which is reliable and reduces the probability the disconnection remaining undetected and causing fatal consequences.

SUMMARY OF THE INVENTION

The present invention is directed to a dialysis system having a disconnection monitor for determining if a blood line connection to a patient has been disconnected, comprising: a blood circuit in fluid communication with a patient and a dialysis circuit; a pressure transducer in pressure communication with the blood circuit wherein the pressure transducer generates a signal indicative of a pulse signal in the blood circuit; a cardiac reference signal generator, wherein the cardiac reference signal generator detects and generates a signal indicative of the patient's pulse and a disconnection monitor. The disconnection monitor comprises a pressure transducer data receiver, wherein the pressure transducer data receiver receives the signal indicative of the pulse signal in the blood circuit; a cardiac reference signal receiver, wherein the cardiac reference signal receiver receives the signal indicative of the patient's pulse; and a processor, wherein the processor cross-correlates the signal indicative of the pulse signal in the blood circuit and the signal indicative of the patient's pulse to generate data indicative of a disconnection of the blood line connection to the patient.

Optionally, the dialysis system comprises a controller, wherein the controller triggers an alarm based upon the data indicative of a disconnection of the blood line connection to the patient. Optionally, the dialysis system comprises a controller, wherein the controller shuts down a dialysis pump based upon the data indicative of a disconnection of the blood line connection to the patient. The pressure transducer non-invasively generates a signal indicative of a pulse signal in the blood circuit. Optionally, along the length of the blood line to the patient, the pressure transducer is separated from the patient by a pinch valve and an air bubble detector.

Optionally, the cardiac reference signal generator is a pulse oximeter. Optionally, the processor cross-correlates the signal indicative of the pulse signal in the blood circuit and the signal indicative of the patient's pulse by computing a sum of products of corresponding pairs of points of the signal indicative of the pulse signal in the blood circuit and the signal indicative of the patient's pulse within a specified time frame. The dialysis system comprises programmatic instructions for directing a patient to first attach said cardiac signal reference generator prior to starting a dialysis pump. The dialysis system comprises programmatic instructions for directing the system to capture the signal indicative of the pulse signal in said blood circuit prior to starting a dialysis pump. The processor comprises an amplifier.

In another embodiment, the present invention is directed toward a dialysis system having a manifold in data communication with a disconnection monitor for determining if a blood line connection to a patient has been disconnected, comprising the disposable manifold having a blood circuit in fluid communication with a patient and a dialysis circuit; a pressure transducer integrated within the manifold and in non-invasive pressure communication with the blood circuit wherein the pressure transducer generates a signal indicative of a pulse signal in the blood circuit; a cardiac reference signal generator, wherein the cardiac reference signal generator detects and generates a signal indicative of the patient's pulse and the disconnection monitor. The disconnection monitor comprises a pressure transducer data receiver, wherein the pressure transducer data receiver receives the signal indicative of the pulse signal in the blood circuit; a cardiac reference signal receiver, wherein the cardiac reference signal receiver receives the signal indicative of the patient's pulse; and a processor, wherein the processor cross-correlates the signal indicative of the pulse signal in the blood circuit and the signal indicative of the patient's pulse to generate data indicative of a disconnection of the blood line connection to the patient.

Optionally, the dialysis system further comprises a controller, wherein the controller triggers an alarm based upon the data indicative of a disconnection of the blood line connection to the patient. The dialysis system further comprises a controller, wherein the controller shuts down a dialysis pump based upon the data indicative of a disconnection of the blood line connection to the patient. The pressure transducer non-invasively generates a signal indicative of a pulse signal in the blood circuit and wirelessly communicates the signal indicative of a pulse signal in said blood circuit to the pressure transducer data receiver. Optionally, the dialysis system, along the length of the blood line to the patient, the pressure transducer is separated from the patient by a pinch valve and an air bubble detector. Optionally, the cardiac reference signal generator is a pulse oximeter and wirelessly communicates the signal indicative of the patient's pulse to the cardiac reference signal receiver.

Optionally, the processor cross-correlates the signal indicative of the pulse signal in the blood circuit and the signal indicative of the patient's pulse by computing a sum of products of corresponding pairs of points of the signal indicative of the pulse signal in the blood circuit and the signal indicative of the patient's pulse within a specified time frame. Optionally, the dialysis system comprises programmatic instructions for directing a patient to first attach said cardiac signal reference generator prior to starting a dialysis pump. Optionally, the dialysis system comprises programmatic instructions for directing the system to capture said signal indicative of the pulse signal in said blood circuit prior to starting a dialysis pump. Optionally, the processor comprises an amplifier.

BRIEF DESCRIPTION OF THE DRAWINGS

The present invention is described by way of embodiments illustrated in the accompanying drawings wherein.

DETAILED DESCRIPTION OF THE INVENTION

The present invention describes an apparatus and method for detection of disconnection in an extracorporeal blood circuit being used for any blood processing treatment routine. Examples of blood processing treatment routines include hemodialysis, hemofiltration, ultrafiltration, apheresis, etc. Vascular access for establishing an extracorporeal blood circuit is typically obtained by using a transdermal needle or a luer connected catheter. The apparatus and method described in the present invention uses the pressure pulse produced by a patient's beating heart as an indicator of an intact needle or catheter connection to the vasculature. The pressure pulse produced by a patient's heart is small; more so, in the venous return line of an extracorporeal blood circuit. In order to detect the small pressure pulse the present invention uses cross correlation methodology wherein a reference cardiac signal is cross correlated to the pressure pulse signal.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention will now be discussed in context of embodiments as illustrated in the accompanying drawings.

Figure 1:
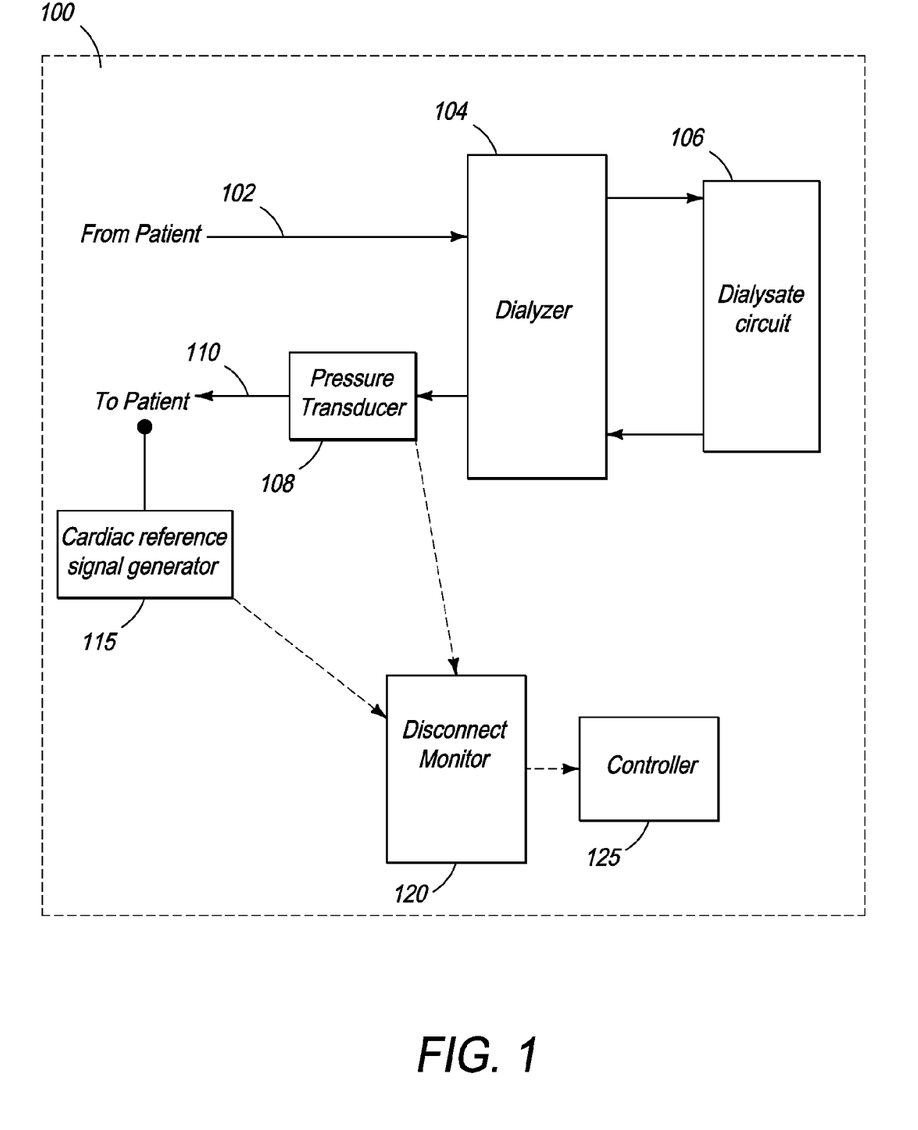
FIG. 1 is a block diagram of a system for detecting a patient's disconnection from an extracorporeal blood circuit, in accordance with an embodiment of the present invention.

FIG. 1 is a block diagram of a system 100 for detecting a patient's disconnection from an extracorporeal blood circuit, in accordance with an embodiment of the present invention. System 100 comprises an incoming arterial blood circuit 102, a dialyzer 104, a dialysate circuit 106, a patient pulse pressure transducer 108, a patient cardiac signal generator 115 for reference, a disconnect monitor 120, a controller 125 and a return venous blood circuit 110. In various embodiments of the present invention, blood drawn from a patient is passed through the dialyzer 104 via the arterial blood circuit 102 and cleansed blood from the dialyzer 104 is returned to the patient via the venous blood circuit 110. Contaminated dialysate expelled from the dialyzer 104 is purified or regenerated within the dialysate circuit 106 and is pumped back into the dialyzer 104. In various embodiments of the present invention, cleansed blood is returned to a patient's body via a transdermal needle or a luer connected catheter. Blood flow rates in the return venous blood circuit 110 are typically in the range of 300-400 ml/min.

It should be appreciated that any suitable dialysis circuit can be deployed. In one preferred embodiment, the dialysis circuit 106 is embodied in a dialysis manifold, as disclosed, in U.S. patent application Ser. No. 12/324,924, filed on Nov. 28, 2008, which has been incorporated herein by reference. In one embodiment, the dialyzer 104 is equivalent to dialyzer 430 of FIG. 4 in U.S. patent application Ser. No. 12/324,924, the venous blood circuit is equivalent to the patient return line of FIG. 4 in U.S. patent application Ser. No. 12/324,924, and the patient pulse pressure transducer is incorporated proximate to Port H 422 of the manifold, such as at pressure transducer 407.

The pressure transducer 108 measures the pressure pulse of a patient undergoing the blood processing treatment routine and communicates the pulse pressure substantially continuously to the disconnect monitor 120. In one embodiment the transducer 108 is an invasive or non-invasive venous pressure sensor located anywhere in the dialysis blood line (the incoming arterial blood circuit 102 or the return venous blood circuit 110). In another embodiment, the transducer 108 is an invasive or non-invasive venous pressure sensor located specifically in a dialysis blood line between the dialyzer 104 and the patient, that is, in the return venous blood circuit 110. A non-invasive air bubble detector and/or pinch valve (not shown) are optionally located between the transducer 108 and the luer connection to the patient. In an embodiment of the present invention, the pressure transducer 108 is located in close proximity to the needle or catheter inserted in the patient's body for providing vascular access corresponding to the return venous blood circuit 110. The pressure transducer 108 is located in close proximity to the needle or catheter in order to preserve waveform fidelity. In other embodiments, the pressure transducer 108 may be connected anywhere in the return venous blood circuit 110. In an embodiment of the present invention, the pressure signal produced by the pressure transducer 108 is an alternating current (AC) signal which is not an accurate measure of vascular pressure. Hence, the pressure transducer 108 is not a high accuracy transducer.

The reference signal generator 115 communicates the patient's cardiac signal substantially continuously to the disconnect monitor 120 for reference. In an embodiment of the present invention, the reference cardiac signal is obtained from a plethysmograph connected to the same body part (such as an arm) to which the needle or catheter supplying processed blood to a patient is connected. In another embodiment of the present invention, the reference cardiac signal is obtained from a finger pulse sensor/oximeter. In various other embodiments of the present invention, the reference cardiac signal may be obtained an electro-cardiogram (ECG) signal, a real time blood pressure signal, stethoscope, arterial pressure signal from the blood withdrawal line, oximeter pulse signal, alternate site plethysmograph signal, transmissive and/or reflective plethysmograph signals, acoustic cardiac signals, wrist pulse or from any other cardiac signal source known to persons of ordinary skill in the art.

The disconnect monitor 120 detects a disruption in the return venous blood circuit 110 caused by the disconnection of a needle or catheter, from the body of a patient undergoing blood processing treatment. To detect a disconnection, the monitor 120 processes the patient pulse pressure transducer and cardiac reference signals. Persons of ordinary skill in the art would appreciate that such disconnection may be caused by the needle or catheter being pulled out of the patient's body due to any reason such as a sudden movement of the patient. The disconnect monitor 108 is described in detail with reference to FIG. 2. Controller 125 is any microprocessor known to persons of ordinary skill in the art. The function of the controller 125 is to receive processed inputs from the monitor 120 and accordingly trigger appropriate actions, when required.

Persons of ordinary skill in the art should appreciate that the pressure transducer and reference signals are communicated to the disconnect monitor 120 through transmitters incorporated into the reference signal generator and pressure transducer. The transmitter can enable a wired or wireless communication to a corresponding receiver. Similarly, data from the disconnect monitor 120 is communicated to the controller 125 through wired or wireless connection. In one embodiment, such signal communication is enabled using an appropriate wired or wireless public and/or private network such as LAN, WAN, MAN, Bluetooth networks, and/or the Internet. Also, in one embodiment the disconnect monitor 120 and controller 125 are located in proximity to each other and to the pressure transducer 108 and the cardiac reference signal generator 115. In an alternate embodiment, both or either of the disconnect monitor 120 and the controller 125 are/is located remotely from each other and/or from the rest of the components of the system 100.

Figure 2:
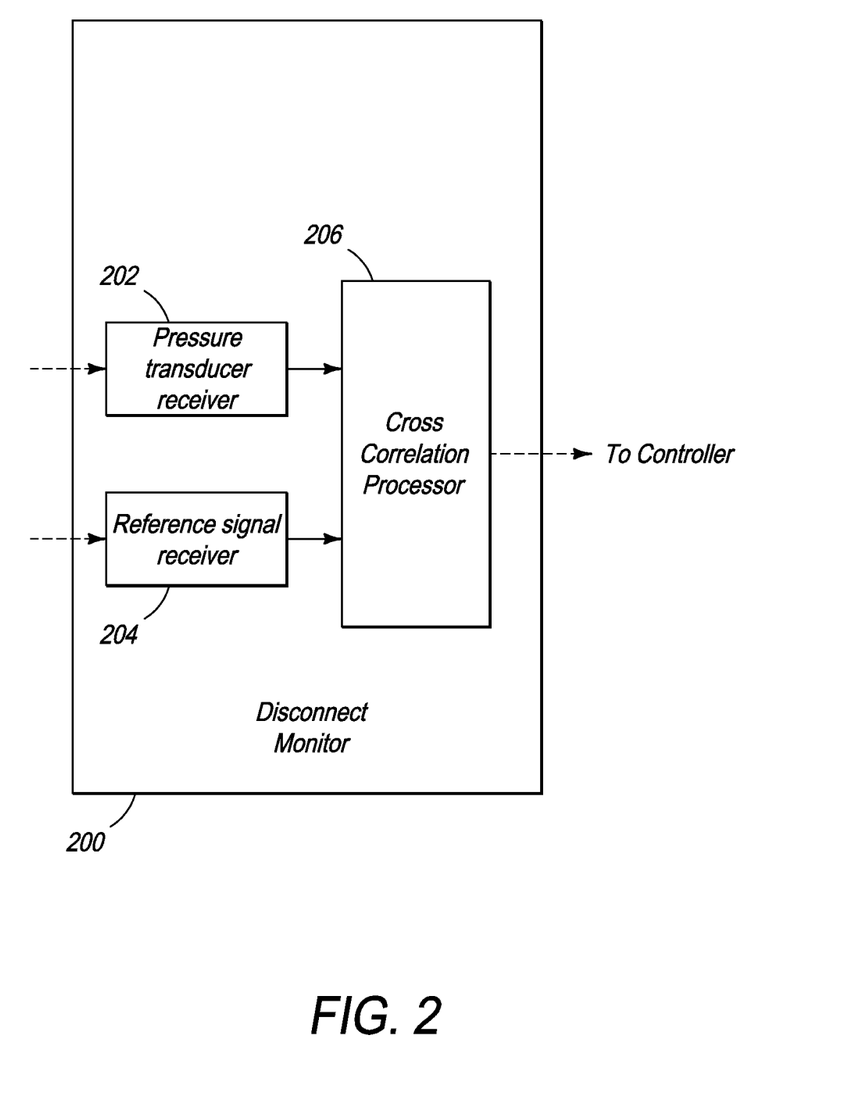
FIG. 2 is a block diagram illustration of an apparatus for detecting disconnection in a return venous blood circuit, in accordance with an embodiment of the present invention.

FIG. 2 is a block diagram illustration of an apparatus 200 for detection of a disconnection in a return venous blood circuit, in accordance with an embodiment of the present invention. The disconnect monitor 200 comprises a pressure transducer receiver 202, a reference signal receiver 204, and a cross correlation processor 206. The transducer receiver 202 and the reference signal receiver 204 receive input signals from the pressure transducer 108 and cardiac reference signal generator 115, respectively, of FIG. 1.

The pressure pulse signal obtained by the pressure transducer receiver 202 and the reference cardiac signal obtained by the reference signal receiver 204 are stored in a local memory and further fed to the cross correlation processor 206, which in turn, computes a correlation between the two signals. The output of the processor 206 is fed into the controller 125 of FIG. 1. If the output produced by the cross correlation processor 206 indicates a correlation between the two input signals, it is inferred that the return venous blood circuit is intact. If the output produced by the cross correlation processor 206 does not indicate a correlation between the two input signals, it is inferred that the return venous blood circuit is broken due to a needle or catheter pull out, and the controller 125 of FIG. 1 triggers appropriate actions, such as sounding an indicative alarm and/or shutting down the dialysis system completely or partially.

Persons of ordinary skill in the art should note that the present invention envisages use of any cross correlation processor that links, corresponds, or otherwise creates a measurable, quantifiable, and/or predictable relationship between the pressure transducer signal and reference signal. In one embodiment of the present invention cross correlation is performed by using a lock in amplifier, such as SR 810 Lock In Amplifier manufactured by Stanford Research Systems, California. Various known techniques for cross correlation detection of very low signal to noise ratio systems, and cardiac signals may be incorporated in the cross correlation processor 206.

In various embodiments of the present invention, the cross correlation function, computed by the cross correlation processor 206, is used to measure the similarities between the two input signals, i.e. the reference cardiac signal and the pressure pulse signal. Computation of the cross correlation function comprises computation of a sum of the products of corresponding pairs of points of the two input signals, within a specified time frame or window. The computation also takes into consideration any potential phase differences between the two input signals by including a lead or lag term. The mathematical formula corresponding to a cross correlation function is represented as:

$$r_{(12)}(j) = \frac{1}{N} \sum_{n=0}^{N-1} x_1(n) x_2(n+j)$$

where N represents a number of samples, j represents a lag factor and x1 and x2 represent the two input signals respectively.

Figure 3:
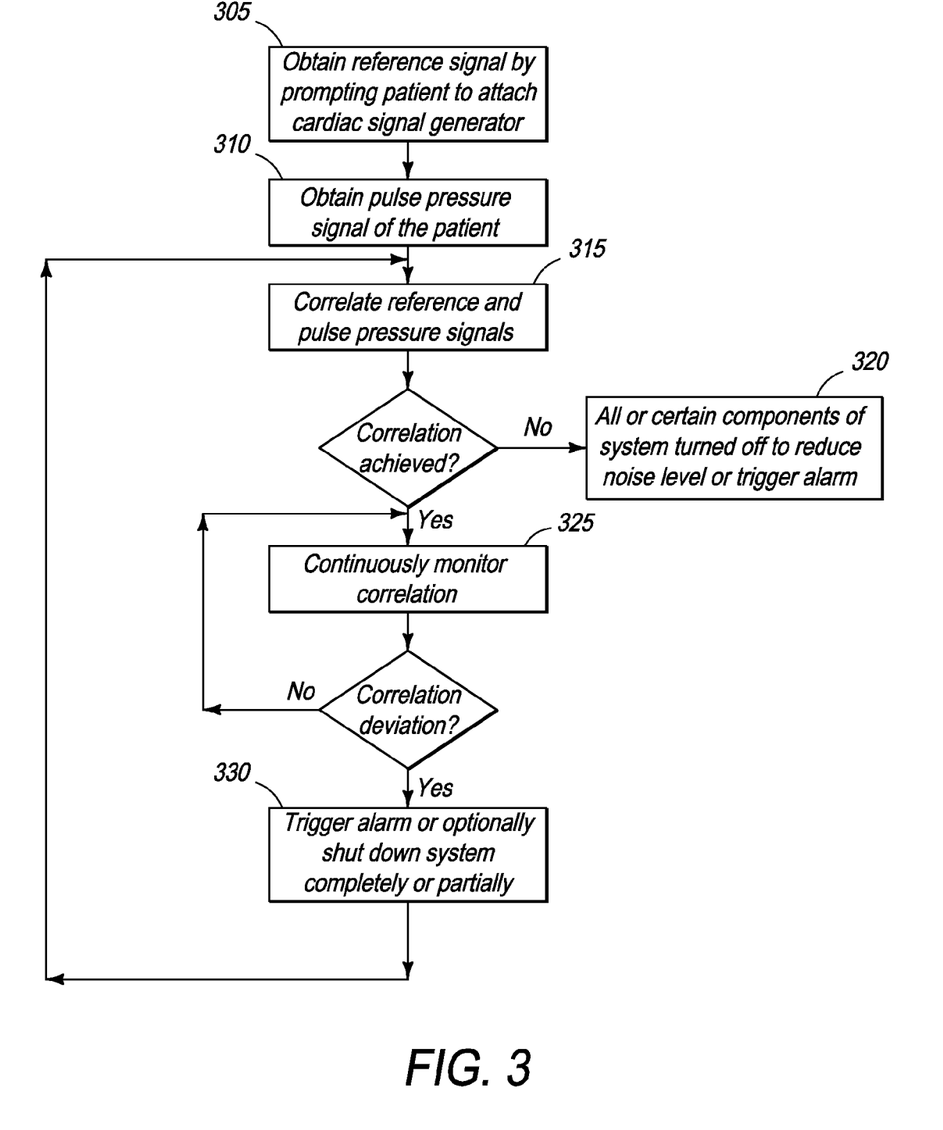
FIG. 3 is a flow diagram showing exemplary steps of a method of ascertaining patient's disconnection from an extracorporeal blood circuit, in accordance with an embodiment of the present invention.

FIG. 3 is a flow diagram showing exemplary steps of a method of ascertaining patient's disconnection from an extracorporeal blood circuit, in accordance with an embodiment of the present invention. In operation, dialysis system software, comprising a plurality of instructions and executing on a processor, prompts a patient to first attach a cardiac signal generator (such as a finger pulse oximeter) to obtain 305 a reference signal. At this point the patient may or may not be connected to a dialysis system. Thereafter or concurrent to capturing the cardiac reference signal, the dialysis system software, comprising a plurality of instructions and executing on a processor, prompts a patient to connect to the system 100 of FIG. 1 as a result of which patient pulse pressure transducer signal is also obtained 310. Next, a cross correlation processor attempts to correlate 315 the reference and transducer signals. If no correlation can be achieved at start-up, in one embodiment, the patient is prompted to turn off 320 all or certain components or, in another embodiment, the controller 125 of the system 100 of FIG. 1 does this automatically to lower noise level. For example, shutting off the pumps of the dialysis system can lower the noise and make it easier to capture and correlate the two signals. In another embodiment, a cross-correlation is attempted before noise-generating system components, such as pumps, are turned on. Thus, lock down of a correlation is attempted before complete system start-up can be completed. In one embodiment, if no correlation is locked down, an alarm is triggered, indicating the patient dialysis system may have an anomaly.

However, if a correlation is obtained, then that correlation is substantially continually monitored 325. If there is any deviation in that correlation, an alarm is triggered 330, indicating a possible leak or, optionally, the system is shut down (completely or partially) and an attempt to re-establish the correlated signal is attempted again. In one embodiment, if the nature of the correlation change or deviates beyond or within a predefined threshold, certain system components, such as pumps, are shut down and the cross correlation processor attempts to re-establish the correlation. If the correlation cannot be re-established, then an alarm is triggered. In another embodiment, if the nature of the correlation change or deviates beyond or outside the range of a predefined threshold, certain system components, such as pumps, are shut down and an alarm is immediately triggered, before any additional attempt to re-establish the correlation.

The present invention provides certain distinct improvements over the prior art. First, unlike the prior art, the present invention is responsive if the needle is just barely pulled out or if it is removed and pulled quite some distance from the insertion site. Second, the present invention does not need any extra apparatus placed at the insertion site, such as a moisture pad. Third, by cross correlating the patients' own cardiac signal, the false negatives are greatly diminished. Fourth, the combination of pressure pulse sensing and cross correlation renders the present invention unique and capable of detecting low signal to noise ratio signals. Fifth, continuously monitoring the cross correlation status enables the system to detect small signal deviations which could potentially indicate a disconnection. Therefore, an apparatus and method for detection of disconnection in an extracorporeal blood circuit being used for any blood processing treatment routine, is provided by the present invention.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A dialysis system having a disconnection monitor for determining if a blood line connection to a patient has been disconnected, comprising:
   a. A blood circuit in fluid communication with a patient and a dialysis circuit;
   b. A pressure transducer in pressure communication with said blood circuit wherein said pressure transducer generates a signal indicative of a pulse signal in said blood circuit;
   c. A cardiac reference signal generator, wherein said cardiac reference signal generator detects and generates a signal indicative of said patient's pulse;
   d. The disconnection monitor comprising:
      i. A pressure transducer data receiver, wherein said pressure transducer data receiver receives said signal indicative of the pulse signal in said blood circuit;

ii. A cardiac reference signal receiver, wherein said cardiac reference signal receiver receives said signal indicative of the patient's pulse; and iii. A processor, wherein said processor cross-correlates said signal indicative of the pulse signal in said blood circuit and said signal indicative of the patient's pulse to generate data indicative of a disconnection of the blood line connection to the patient.

2. The dialysis system of claim 1 further comprising a controller, wherein said controller triggers an alarm based upon said data indicative of a disconnection of the blood line connection to the patient.

3. The dialysis system of claim 1 further comprising a controller, wherein said controller shuts down a dialysis pump based upon said data indicative of a disconnection of the blood line connection to the patient.

4. The dialysis system of claim 1 wherein said pressure transducer non-invasively generates a signal indicative of a pulse signal in said blood circuit.

5. The dialysis system of claim 4 wherein, along the length of said blood line to said patient, said pressure transducer is separated from said patient by a pinch valve and an air bubble detector.

6. The dialysis system of claim 1 wherein the cardiac reference signal generator is a pulse oximeter.

7. The dialysis system of claim 1 wherein the processor cross-correlates said signal indicative of the pulse signal in said blood circuit and said signal indicative of the patient's pulse by computing a sum of products of corresponding pairs of points of the signal indicative of the pulse signal in said blood circuit and said signal indicative of the patient's pulse within a specified time frame.

8. The dialysis system of claim 1 further comprising programmatic instructions for directing a patient to first attach said cardiac signal reference generator prior to starting a dialysis pump.

9. The dialysis system of claim 1 further comprising programmatic instructions for directing the system to capture said signal indicative of the pulse signal in said blood circuit prior to starting a dialysis pump.

10. The dialysis system of claim 1 wherein the processor comprises an amplifier.

11. A dialysis system having a manifold in data communication with a disconnection monitor for determining if a blood line connection to a patient has been disconnected, comprising:

a. The disposable manifold having a blood circuit in fluid communication with a patient and a dialysis circuit;

b. A pressure transducer integrated within said manifold and in non-invasive pressure communication with said blood circuit wherein said pressure transducer generates a signal indicative of a pulse signal in said blood circuit;

c. A cardiac reference signal generator, wherein said cardiac reference signal generator detects and generates a signal indicative of said patient's pulse;

d. The disconnection monitor comprising:

i. A pressure transducer data receiver, wherein said pressure transducer data receiver receives said signal indicative of the pulse signal in said blood circuit;

ii. A cardiac reference signal receiver, wherein said cardiac reference signal receiver receives said signal indicative of the patient's pulse; and iii. A processor, wherein said processor cross-correlates said signal indicative of the pulse signal in said blood circuit and said signal indicative of the patient's pulse to generate data indicative of a disconnection of the blood line connection to the patient.

12. The dialysis system of claim 11 further comprising a controller, wherein said controller triggers an alarm based upon said data indicative of a disconnection of the blood line connection to the patient.

13. The dialysis system of claim 11 further comprising a controller, wherein said controller shuts down a dialysis pump based upon said data indicative of a disconnection of the blood line connection to the patient.

14. The dialysis system of claim 11 wherein said pressure transducer non-invasively generates a signal indicative of a pulse signal in said blood circuit and wirelessly communicates said signal indicative of a pulse signal in said blood circuit to the pressure transducer data receiver.

15. The dialysis system of claim 14 wherein, along the length of said blood line to said patient, said pressure transducer is separated from said patient by a pinch valve and an air bubble detector.

16. The dialysis system of claim 11 wherein the cardiac reference signal generator is a pulse oximeter and wirelessly communicates said signal indicative of the patient's pulse to the cardiac reference signal receiver.

17. The dialysis system of claim 11 wherein the processor cross-correlates said signal indicative of the pulse signal in said blood circuit and said signal indicative of the patient's pulse by computing a sum of products of corresponding pairs of points of the signal indicative of the pulse signal in said blood circuit and said signal indicative of the patient's pulse within a specified time frame.

18. The dialysis system of claim 11 further comprising programmatic instructions for directing a patient to first attach said cardiac signal reference generator prior to starting a dialysis pump.

19. The dialysis system of claim 11 further comprising programmatic instructions for directing the system to capture said signal indicative of the pulse signal in said blood circuit prior to starting a dialysis pump.

20. The dialysis system of claim 11 wherein the processor comprises an amplifier.

* * * * *